(12) United States Patent
Motoki (10) Patent No.: US 9,101,331 B2
(45) Date of Patent: Aug. 11, 2015

(54) OBJECT INFORMATION ACQUIRING APPARATUS AND CALIBRATION DEVICE

(71) Applicant: CANON KABUSHIKI KAISHA, Tokyo (JP)

(72) Inventor: Yohei Motoki, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 340 days.

(21) Appl. No.: 13/778,680

(22) Filed: Feb. 27, 2013

(65) Prior Publication Data

US 2013/0237799 A1   Sep. 12, 2013

(30) Foreign Application Priority Data

Mar. 9, 2012  (JP) .................. 2012-053181

(51) Int. Cl.
  *G01M 1/14*  (2006.01)
  *A61B 6/00*  (2006.01)
  *A61B 5/00*  (2006.01)

(52) U.S. Cl.
  CPC .............. *A61B 6/583* (2013.01); *A61B 5/0095* (2013.01); *A61B 5/708* (2013.01); *A61B 2560/0228* (2013.01)

(58) Field of Classification Search
  CPC ......... G01F 21/00; G01F 23/50; G01N 29/30; G01N 9/08; A61B 19/5244
  USPC ............ 73/1.1, 1.82, 310, 407, 437; 600/407; 367/13
  See application file for complete search history.

(56) References Cited

U.S. PATENT DOCUMENTS

| 3,741,003 A * | 6/1973 | Gunkel ........................... 73/637 |
| 7,665,364 B2 * | 2/2010 | Su et al. ......................... 73/643 |
| 7,864,307 B2 * | 1/2011 | Fukutani et al. ................ 356/73 |
| 2011/0112391 A1 * | 5/2011 | Nishihara et al. ............. 600/407 |

FOREIGN PATENT DOCUMENTS

JP    2009-101193    5/2009

* cited by examiner

*Primary Examiner* — Lisa Caputo
*Assistant Examiner* — Nigel Plumb
(74) *Attorney, Agent, or Firm* — Fitzpatrick, Cella, Harper & Scinto (57) ABSTRACT

The present invention employs an object information acquiring apparatus that receives an acoustic wave generated from an object, on which light is irradiated, and generates property information. The apparatus includes a housing including an aperture into which, when the acoustic wave is received, the object, which is a part of an examinee, is inserted and, when performance evaluation for the apparatus is performed, a calibration device corresponding to a type of the performance evaluation is inserted, the housing being capable of holding the examinee; a holding unit configured to hold the object; a positioning unit configured to specify an attachment position of the calibration device correspondingly to a position specifying member of the calibration device; and a detecting unit configured to detect the type of the performance evaluation performed using the inserted calibration device.

15 Claims, 7 Drawing Sheets

|  | SENSOR 1 | SENSOR 2 | SENSOR 3 |
|---|---|---|---|
| NORMAL | OFF | OFF | OFF |
| CALIBRATION DEVICE 1 | ON | ON | ON |
| CALIBRATION DEVICE 2 | ON | ON | OFF |
| CALIBRATION DEVICE 3 | ON | OFF | OFF |
| CALIBRATION DEVICE 4 | ON | OFF | ON |
| CALIBRATION DEVICE 5 | OFF | ON | ON |
| CALIBRATION DEVICE 6 | OFF | OFF | ON |
| ... |  |  |  |

FIG. 6

OBJECT INFORMATION ACQUIRING APPARATUS AND CALIBRATION DEVICE

BACKGROUND OF THE INVENTION

1. Field of the Invention

The present invention relates to an object information acquiring apparatus and a calibration device.

2. Description of the Related Art

As one of imaging techniques for irradiating light on an object such as a living organism from a light source such as a laser, and converting information concerning the inside of the living organism obtained on the basis of incident light into an image, photoacoustic imaging technique has been proposed. The photoacoustic imaging is a technique for irradiating pulsed light generated from the light source on the living organism, receiving an acoustic wave generated from a biological tissue that has absorbed light propagating and diffusing in the living organism, and subjecting the received acoustic wave to analysis processing to visualize information concerning the inside of the living organism, which is the object.

As the object, a living organism, specifically, a target region of diagnosis such as a breast, a finger, or a limb of a human body or an animal is assumed. A light absorber on the inside of the object relatively has a high absorption coefficient in the object. For example, when a human body is a measurement target, oxygenated or reduced hemoglobin, a blood vessel including a large quantity of the hemoglobin, or a malignant tumor including a large number of newborn blood vessels corresponds to the light absorber. Consequently, it is possible to obtain an optical characteristic distribution in the living organism, in particular, a light absorption coefficient distribution and an oxygen saturation distribution. Researches for diagnosing the object using an image of the light absorption coefficient distribution or the like have been performed.

In a medical diagnostic apparatus such as an X-ray CT apparatus, an MRI apparatus, a nuclear medicine diagnostic apparatus, an ultrasound diagnostic apparatus, or a PET-CT apparatus, a biological tissue model called human body tissue stimulant material (phantom) is used in order to perform performance evaluation and calibration in a scene such as inspection of the apparatus. As a material of the phantom, a material close to characteristics of the human body tissue and a material that can be stored for a long period without causing, for example, proliferation of unwanted bacteria are demanded. The phantom is set in the medical diagnostic apparatus and scanned to collect data. Then, performance evaluation is performed from the collected data and a calibration place and a calibration amount are searched.

The phantom is manually set in an image pickup setting region when the performance evaluation or calibration of the medical diagnostic apparatus is performed. Therefore, a position and a tilt for setting the phantom are different every time. Therefore, positional deviation or the like of a captured image occurs and accuracy of a measured image cannot be guaranteed. It is also attempted to affix a mark to an image pickup region with a tape or the like and place the phantom in a fixed position as much as possible. However, since a setting person only sets the phantom according to his or her senses while visually checking the mark, it is difficult to strictly manage the setting of the phantom. Therefore, as a method of accurately setting the phantom, there is proposed a positioning method for fixing a positioning frame size using a plurality of pins in a calibration device for the phantom (Japanese Patent Application Laid-Open No. 2009-101193).

Patent Literature 1: Japanese Patent Application Laid-Open No. 2009-101193

SUMMARY OF THE INVENTION

However, in a photoacoustic diagnostic apparatus, besides the calibration by the phantom, it is necessary to perform performance evaluation for a light amount distribution, an irradiation density distribution, and the like in order to accurately calculate an oxygen saturation distribution and a light absorption coefficient distribution. In this case, likewise, positional deviation from a measurement instrument occurs and the light amount distribution, the irradiation density distribution, and the like cannot be accurately measured. Further, when there are various types of performance evaluation, an operator needs to perform work by switching a system according to performance that has to be calibrated. Therefore, the work is complicated.

The present invention has been devised in view of the problems and it is an object of the present invention to provide a technique for facilitating handling of an evaluation member for performing performance evaluation for an apparatus that performs photoacoustic measurement.

The present invention provides an object information acquiring apparatus that receives an acoustic wave generated from an object, on which light is irradiated, and generates property information of an inside of the object, the object information acquiring apparatus comprising:

a housing including an aperture into which, when the acoustic wave is received, the object, which is a part of an examinee, is inserted and, when performance evaluation for the object information acquiring apparatus is performed, a calibration device corresponding to a type of the performance evaluation is inserted, the housing being capable of holding the examinee;

a holding unit configured to hold the object;

a positioning unit configured to specify an attachment position of the calibration device correspondingly to a position specifying member provided in the calibration device inserted into the aperture; and a detecting unit configured to detect the type of the performance evaluation performed using the calibration device inserted into the aperture.

The present invention also provides a calibration device for performing performance evaluation for an object information acquiring apparatus that receives an acoustic wave generated from an object, on which light is irradiated, and generate property information of an inside of the object, the calibration device being inserted from an aperture provided in a housing of the object information acquiring apparatus, the calibration device comprising:

a position specifying member configured to specify a position of the calibration device in the object information acquiring apparatus, correspondingly to a positioning unit provided in the object information acquiring apparatus;

an evaluation member corresponding to a type of the performance evaluation; and a type specifying member that can be attached according to the type of the performance evaluation and that corresponds to a detecting unit provided in the object information acquiring apparatus.

According to the present invention, it is possible to provide a technique for facilitating handling of an evaluation member for performing performance evaluation for an apparatus that performs photoacoustic measurement.

Further features of the present invention will become apparent from the following description of exemplary embodiments with reference to the attached drawings.

DESCRIPTION OF THE EMBODIMENTS

Preferred embodiments of the present invention are explained below with reference to the drawings. However, dimensions, materials, and shapes of components explained below, relative arrangement of the components, and the like should be changed as appropriate according to the configuration of an apparatus to which the present invention is applied and various conditions and are not meant to limit the scope of the present invention to the below description.

A photoacoustic diagnostic apparatus according to the present invention includes an apparatus that makes use of a photoacoustic effect for irradiating light (an electromagnetic wave) on an object to thereby receive an acoustic wave generated in the object and acquiring property information of the inside of the object as image data. The property information acquired at this point indicates a generation source distribution of the acoustic wave caused by the light irradiation, an initial sound pressure distribution in the object, an optical energy absorption density distribution and an absorption coefficient distribution derived from the initial sound pressure distribution, or a concentration distribution of a substance that forms a tissue. The concentration distribution of the substance is, for example, an oxygen saturation distribution or an oxygenated or reduced hemoglobin concentration distribution. Since such property information is referred to as object information as well, the photoacoustic diagnostic apparatus according to the present invention can be referred to as object information acquiring apparatus as well.

The acoustic wave in the present invention is typically an ultrasound wave and includes an elastic wave referred to as sound wave, ultrasound wave, or acoustic wave. The acoustic wave caused by the photoacoustic effect is referred to as photoacoustic wave or light-induced ultrasound wave. An acoustic wave probe of the object information acquiring apparatus receives the acoustic wave generated in the object.

<First Embodiment>

Figure 1A:
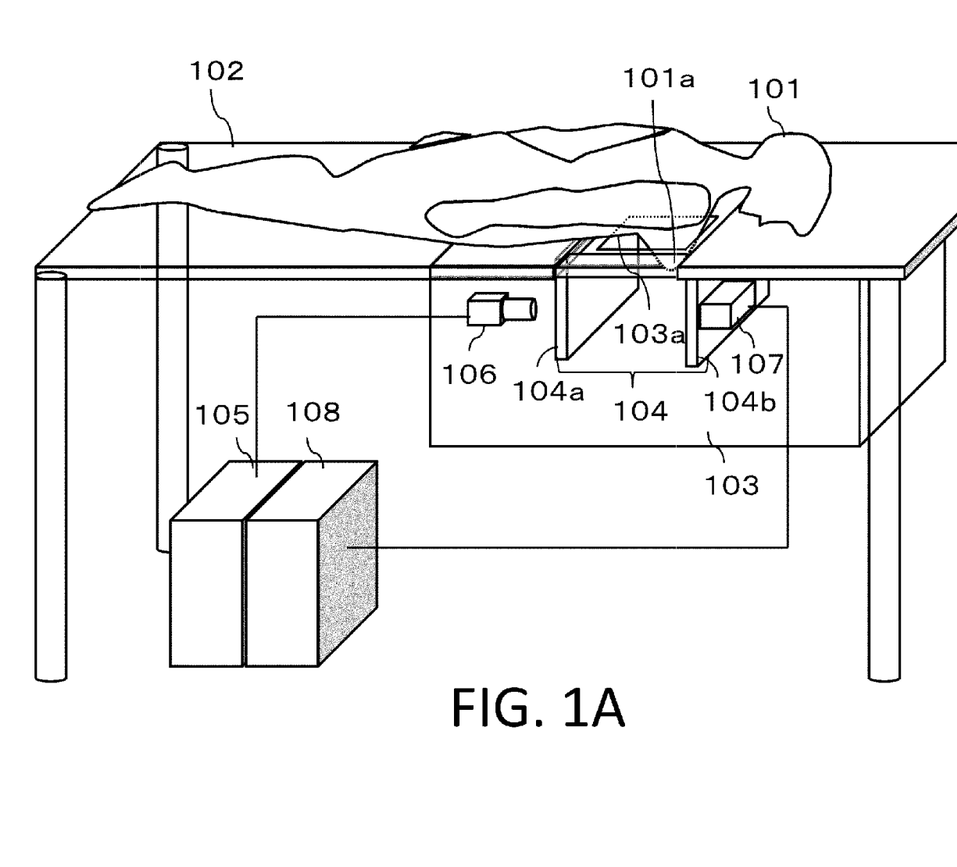
FIG. 1A is a schematic diagram showing an example of a photoacoustic diagnostic apparatus in a first embodiment.
Figure 1B:
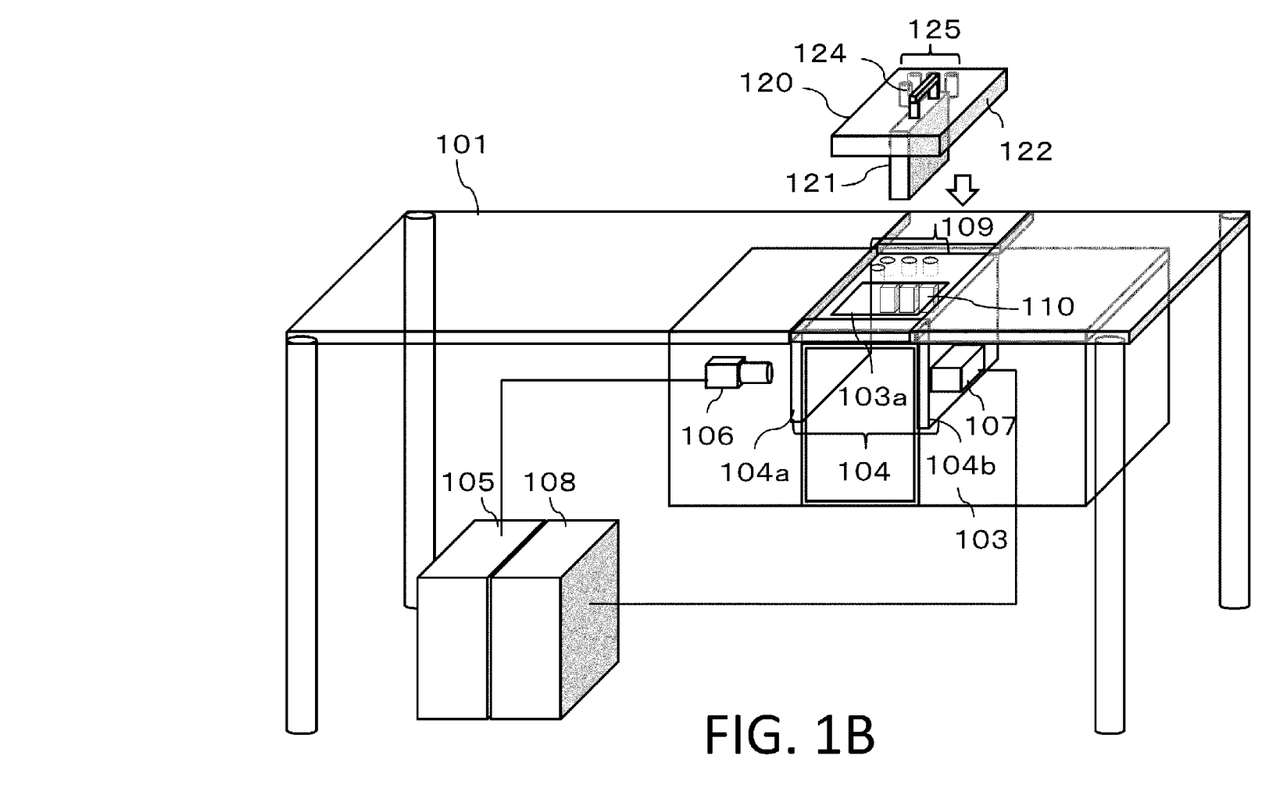
FIG. 1B is another schematic diagram showing the example of the photoacoustic diagnostic apparatus in the first embodiment.

An embodiment to which the present invention is applied is explained below with reference to FIGS. 1A and 1B to 3 and 6. FIGS. 1A and 1B are schematic diagrams showing an example of the configuration of a photoacoustic diagnostic apparatus in this embodiment.

FIG. 1A is a schematic diagram of an examination of an examinee 101 in the photoacoustic diagnostic apparatus. The examinee 101 lies on a bed 102 in a prone position and inserts an object 101a, which is a part of the examinee, into an aperture 103a of a housing 103. As the object 101a, the breast of the examinee is assumed. However, the object 101a is not limited to this. The object 101a is inserted between a movable holding member 104a and a fixed holding member 104b of a holding unit 104 and sandwiched according to the movement of the movable holding member 104a.

After the object 101a is held, light (pulsed light) generated by a light source 105 is irradiated on the object 101a by an irradiating unit 106 via the movable holding member 104a. A light absorber (a detection target such as a tumor) in the object 101a on which the light is irradiated absorbs optical energy and generates an acoustic wave according to the photoacoustic effect. The generated acoustic wave propagates in the object 101a and reaches an acoustic wave probe 107 via the fixed holding member 104b. The acoustic wave probe 107 receives the acoustic wave, converts the acoustic wave into an electric signal, and outputs the electric signal to a calculating unit 108. The calculating unit 108 performs signal processing and control of regions in the apparatus. The calculating unit 108 generates property information of the inside of the object 101a using the input electric signal, generates photoacoustic image data on the basis of the property information, and causes a display unit (not shown in the figure) to display an image of the photoacoustic image data.

As explained above, in the photoacoustic diagnostic apparatus, various functions are combined to generate the property information of the inside of the object 101a. Therefore, performance evaluation and calibration need to be performed concerning the functions. Concerning a period of the performance evaluation, for example, it is conceivable to evaluate, after the apparatus is used for a considerable period, whether any difference occurs from an initial state because of the elapse of time and perform calibration if a difference occurs. Besides, it is also conceivable to evaluate, in an initial state before shipment or operation of the apparatus, whether necessary performance is satisfied or performance is shown as designed.

An example of the performance evaluation is explained below. First, a state of irradiation light between the movable holding member 104a and the fixed holding member 104b needs to be subjected to the performance evaluation. The state of the irradiation light, for example, an amount and density of light irradiated on the object 101a and distributions of the amount and the density of the light are information necessary in calculating the property information. Therefore, if these values are inaccurate, an image of the object 101a to be generated is inaccurate and likely to adversely affect diagnosis.

The performance evaluation is performed concerning the accuracy of an acoustic wave acquired by the acoustic wave probe 107 as well. The accuracy of the acoustic wave is likely to be deteriorated by various factors such as a hindrance factor in a path of the acoustic wave, reception sensitivity of the acoustic wave probe 107, and performance of a circuit or the like that processes an electric signal after reception. Therefore, the performance evaluation is necessary. By performing the performance evaluation, it is possible to accurately calculate the intensity, the direction, and the like of the generated acoustic wave and acquire a satisfactory image.

For example, when a result of the performance evaluation deviates from a standard, it is necessary to enable calibration by an operator and perform automatic calibration. As members necessary for the performance evaluation and the calibration, there are various members such as a phantom that performs performance check for the photoacoustic diagnostic apparatus and a light distribution measuring device and a luminance distribution measuring device that measure a state of light irradiated on the object 101a.

When actual performance evaluation and calibration are performed, members (collectively referred to as calibration device) used for the performance evaluation and the calibration are inserted into a place between the holding members where the object 101a is originally inserted. FIG. 1B is a schematic diagram of the performance evaluation and the calibration for the photoacoustic diagnostic apparatus performed using the calibration device. As shown in FIG. 1B, a calibration device 120 is inserted instead of the object 101a shown in FIG. 1A.

FIG. 1B is a diagram showing a state in which the calibration device 120 is attached to the aperture 103a of the housing 103. The calibration device 120 includes position specifying members for accurately attaching the calibration device 120. The position specifying members in this embodiment are positioning pins 124. On the other hand, a positioning unit 109 combined with the position specifying members to accurately define an attachment position is provided in the vicinity of the aperture 103a of the housing 103. The positioning unit 109 in this embodiment is a plurality of holes provided in the housing 103. In positioning, the position specifying members of the calibration device 120 are inserted into the positioning unit 109 of the housing 103.

A plurality of detecting members 110 for detecting a type of the calibration device 120 are present right under the holes, which are the positioning unit 109 of the housing 103. The detecting members 110 are equivalent to a detecting unit of the present invention. The calibration device 120 includes a type specifying member for specifying what type of an evaluation member the calibration device 120 includes. The detection members 110 detect a type of the performance evaluation on the basis of the type specifying member and output a signal corresponding to the type to the calculating unit 108. Then, the calculating unit 108 automatically switches a system according to the type of the performance evaluation. A specific combination of the detecting unit and the type specifying member is explained in embodiments below.

The configuration of the photoacoustic diagnostic apparatus according to this embodiment is specifically explained below.

The housing 103 is a member having a size and intensity enough for holding an examinee. The housing 103 includes the aperture 103a for inserting an object of the examinee. The housing 103 desirably has structure for blocking light other than light from the aperture 103a. For the housing 103, it is desirable to use a metal material such as aluminum, magnesium, or iron that does not transmit a laser. Alternatively, the laser can be blocked by sticking a metal film to carbon, resin, or the like. The aperture 103a may have any shape as long as the aperture 103a has a size enough for inserting the object 101a.

The holding unit 104 includes the fixed holding member 104b and the movable holding member 104a. The holding unit 104 can hold the object between the two holding members. It is possible to keep constant the shape of at least a part of the object by holding the object with the two holding members. When the object is sandwiched from both the sides as shown in FIG. 1A, since the position of the object is fixed, it is possible to reduce the influence of body movement and the like. It is possible to press the object and reduce the thickness of the object by reducing the distance between the holding members that hold the object. Therefore, it is possible to efficiently allow light to reach the depth. As the movable holding member 104a on the side where the irradiating unit 106 is provided, a member having high light transmittance is desirable. As the fixed holding member 104b on the side where the acoustic wave probe 107 is provided, a member having a high acoustic matching property with the object and the acoustic wave probe 107 is desirable. An acoustic matching member such as gel may be interposed between the holding unit 104 and the object for the purpose of improving the acoustic matching property. A positional relation between the fixed holding member 104b and the movable holding member 104a is not limited to a positional relation shown in FIG. 1A. The irradiating unit side may be fixed or both the irradiating unit side and the acoustic wave probe side may be movable.

The light source 105 includes at least one coherent or incoherent pulsed light source. In order to cause the photoacoustic effect, pulse width is desirably equal to or smaller than several hundred nanoseconds and more desirably in a range of 5 nsec to 50 nsec. When a breast cancer or the like is measured, light having specific wavelength absorbed by a specific component (e.g., hemoglobin) among components forming a living organism is irradiated. Specifically, wavelength equal to or larger than 500 nm and equal to or smaller than 1200 nm is desirable. As the light source 105, a laser that can obtain a large output is desirable. However, it is also possible to use a light-emitting diode instead of the laser. As the laser, various lasers such as a solid-state laser, a gas laser, a dye laser, and a semiconductor laser can be used. For example, an Nd:YAG laser or a Ti:sapphire laser can be used. The wavelength may be variable.

The irradiating unit 106 includes an optical system such as a mirror that reflects light, a half mirror for splitting light into reference light and irradiation light, a lens that condenses and magnifies light or changes a shape, and an optical waveguide. The optical system may be any optical system as long as the optical system can irradiate light, which is emitted from the light source 105, on the object in a desired shape. It is preferable to spread the light to a certain degree of area by diffusing the light with the lens. Consequently, it is possible to satisfy a safety standard and further improve efficiency of measurement. In order to irradiate the light in a wide range, it is desirable that a region where the light is irradiated on the object can move on the object. As a method of moving the region where the light is irradiated on the object, there are, for example, a method of using a movable mirror or the like and a method of mechanically moving the light source 105 itself. The irradiating unit 106 may be integrated with the holding unit 104.

The acoustic wave probe 107 includes one or more elements that receive an acoustic wave and convert the acoustic wave into an electric signal. The element may be any element such as a transducer that makes use of a piezoelectric effect, a transducer that makes use of resonance of light, or a transducer that makes use of a change in a capacity as long as the element can receive the acoustic wave and convert the acoustic wave into an electric signal. It is possible to simultaneously receive the acoustic wave in a plurality of places by one-dimensionally or two-dimensionally arraying a plurality of the elements that receive the acoustic wave. Therefore, it is possible to reduce a reception time and reduce the influence of, for example, vibration of the object. By moving one element, it is also possible to obtain a signal same as a signal obtained when the plurality of elements are one-dimensionally or two-dimensionally arranged. The acoustic wave probe 107 is provided on the fixed holding member side in FIGS. 1A and 1B. However, the acoustic wave probe 107 may be provided on the movable holding member side.

As the calculating unit 108, a workstation or the like is typically used. For example, processing for calculating a light irradiation density distribution and feeding back a result of the calculation to irradiation light is performed by software programmed in advance. The calculating unit 108 applies noise reduction processing or the like to an electric signal captured from the acoustic wave probe 107. Further, the calculating unit 108 performs overall processing for causing the photoacoustic diagnostic apparatus to operate such as control of a scanning mechanism.

During the performance evaluation for the photoacoustic diagnostic apparatus, a type of the calibration device 120 inserted from the aperture 103a is detected by the detecting members 110. The system is automatically switched according to a target of the performance evaluation.

The positioning unit 109 is provided in the vicinity of the aperture 103a of the housing 103 in order to accurately define, in a predetermined position, the calibration device 120 used for the performance evaluation and the calibration. The positioning unit 109 is set in a position where the positioning unit 109 does not obstruct the measurement of the object. For example, the positioning unit 109 is desirably set in a position where the positioning unit 109 does not f hinder the movement of the holding member that presses and holds the object and the traveling of light and an acoustic wave. The positioning unit 109 desirably includes a plurality of fitting sections for fitting with the position specifying members of the calibration device 120. For example, the positioning unit 109 shown in FIG. 1B is circular holes and is formed in a shape corresponding to and fit with the positioning pins 124, which are the position specifying members of the calibration device 120. Besides, the positioning unit 109 may have any shape such as a square, a hexagon, a star shape, or the like as long as the positioning unit 109 can fit with the position specifying members. The holes do not need to be perforated and only have to be deeper than the length of the positioning pins 124 of the position specifying members and detection pins 125 of the calibration device 120.

The detecting members 110 are provided correspondingly to the calibration device 120. An appropriate detecting method is decided according to the detecting member 110. For example, when sensors such as switches that are pressed to be turned on and off are used as the detecting members 110, a projecting section is provided in the calibration device 120 as the type specifying member. A type of the performance evaluation is specified according to which switch is pressed by the projecting section. When sensors that detect a contact or a load are used as the detecting members 110, likewise, the type of the performance evaluation is specified. When sensors that detect light are used as the detecting members 110, a light such as an LED may be provided as the type specifying member of the calibration device 120 or light from the outside may be led in. When a camera is used as the detecting members 110, information that can specify the type of the performance evaluation may be described in a predetermined position photographed by the camera in the calibration device 120 and may be specified by, for example, image recognition by the calculating unit 108. Members such as readable IC chips may be set in the calibration device 120 and the detecting members 110 may read the members. Besides, as the detecting members 110, any members may be used as long as the members can detect the type of the calibration device 120.

The detecting members 110 in this embodiment are a plurality of set switches. The type of the performance evaluation can be specified according to a combination of ON and OFF of the detecting members 110. A place where the detecting members 110 are set is a position corresponding to the calibration device 120. The type of the performance evaluation in this embodiment is specified by the detection pins 125, which are the type specifying member. Therefore, the detecting members 110 are set in all positions where the detection pins 125 could be arranged.

The calibration device 120 includes an evaluation member 121 for the performance evaluation and the calibration, an attachment member 123 (not shown in the figure) that fixes the evaluation member 121, and a setting section 122 for attaching the calibration device 120 to the photoacoustic diagnostic apparatus. The setting section 122 includes position specifying members for positioning the calibration device 120 on the bed. That is, the positioning pins 124 are set to project in predetermined positions of the setting section 122. One or more detection pins 125 are also set to project from the setting section 122. At this point, one or more of the positioning pins 124 can be used as detection pins. It is possible to reduce the number of members by using the same pins as both of the positing pins 124 and the detection pins 125.

In the type specifying member, the number and the arrangement of the detection pins 125 can be varied according to a type of the evaluation member 121, i.e., a type of the performance evaluation. The detection members 110 specify the evaluation member 121 according to a combination of the detection pins 125. There is no limitation in the array and the number of the positioning pins 124 and the detection pins 125. The array and the number of the positioning pins 124 and the detection pins 125 may be freely combined. By configuring the detection pins 125 to be replaceable, it is possible to simultaneously replace the detection pins 125 when the evaluation member 121 is replaced and cause the calculating unit 108 to recognize what type of the performance evaluation is performed.

A plurality of types of the evaluation member 121 can be replaced. The evaluation member 121 is attached according to a target of the performance evaluation and the calibration. As the evaluation member 121, there are a phantom, a measuring device for a state of light, a measuring device for a load, and the like. Besides a system in which the calibration device 120 includes the attachment member 123 and the evaluation member 121 is replaced according to the type of the performance evaluation, a system in which the entire calibration device 120 is replaced for each type of the performance evaluation may be used.

The phantom is mainly used for calibration of measurement accuracy of the photoacoustic diagnostic apparatus. The phantom, a material and an optical or acoustic characteristic of which are known, is measured, whereby it is possible to evaluate measurement accuracy and performance of property information generation. As the phantom, for example, there are a phantom for accuracy management for photoacoustic matching and a phantom for accuracy management for acoustic matching. The phantoms for the photoacoustic matching and the acoustic matching may be separate or may be integral. The phantom for the photoacoustic matching is created with an optical characteristic simulated to an optical characteristic of a biological tissue such as a human body. The phantom for the acoustic matching is created with an acoustic characteristic simulated to an acoustic characteristic of the biological tissue such as the human body. As a material of the phantom, a material that is close to a characteristic of a human body tissue and can be stored for a long period without causing, for example, proliferation of unwanted bacteria is desirable.

The measuring device for a state of irradiated light, for example, the measuring device for a light amount distribution and an irradiation density distribution is used to accurately calculate an oxygen saturation distribution and a light absorption coefficient distribution. Any measuring devices may be used as long as the measuring device can measure a light amount distribution and a luminance distribution like an optical sensor such as an illuminometer or a photomultiplier. By measuring irradiation density of light and a light amount, it is possible to evaluate whether light irradiated on the object matches a safety standard. As the safety standard, for example, maximum permissible exposure (MPE) is used.

The measurement of a load is used to calibrate a value of a sensor (not shown) that measures a load acting when the object is sandwiched between the movable holding member 104a and the fixed holding member 104b included in the holding unit 104. As the measuring device for calibrating the load, any measuring device may be used as long as the measuring device can accurately detect a load such as a load cell and a strain gauge.

Further, a calibration device for full maintenance that can execute all the types of the performance evaluation explained above may be manufactured. Consequently, replacement work for the evaluation member 121 is unnecessary. It is possible to reduce the likelihood of positional deviation of the calibration device. Further, it is possible to flexibly set types, order, and the like of types of the performance evaluation that are simultaneously carried out.

In a state in which the calibration device 120 is attached, it is desirable that the setting section 122 completely blocks the aperture 103a of the housing 103. Consequently, it is possible to improve safety of the operator or the examinee against the laser emitted from the light source 105. A material that does not transmit the laser is used for the setting section 122. A metal material such as aluminum, magnesium, or iron is particularly suitably used. Besides, a material that absorbs wavelength of light of a light source used in a light source unit may be used or a metal film may be stuck to carbon or resin and used.

Convenience during transportation and attachment to a housing is improved by providing a handle in the calibration device 120. The shape of the setting section 122 does not always need to be a rectangular shape and may be any shape such as a circular shape or a hexagonal shape as long as the dead load of the calibration device 120 can be supported. The setting section 122 does not always have to have a plate-like shape. A shape that blocks the aperture 103a and can be easily handled is desirable. The evaluation member 121 does not always need to be set in the calibration device 120. The calibration device 120 may be used to limit the functions of the photoacoustic diagnostic apparatus making use of the setting section 122.

Figure 2:
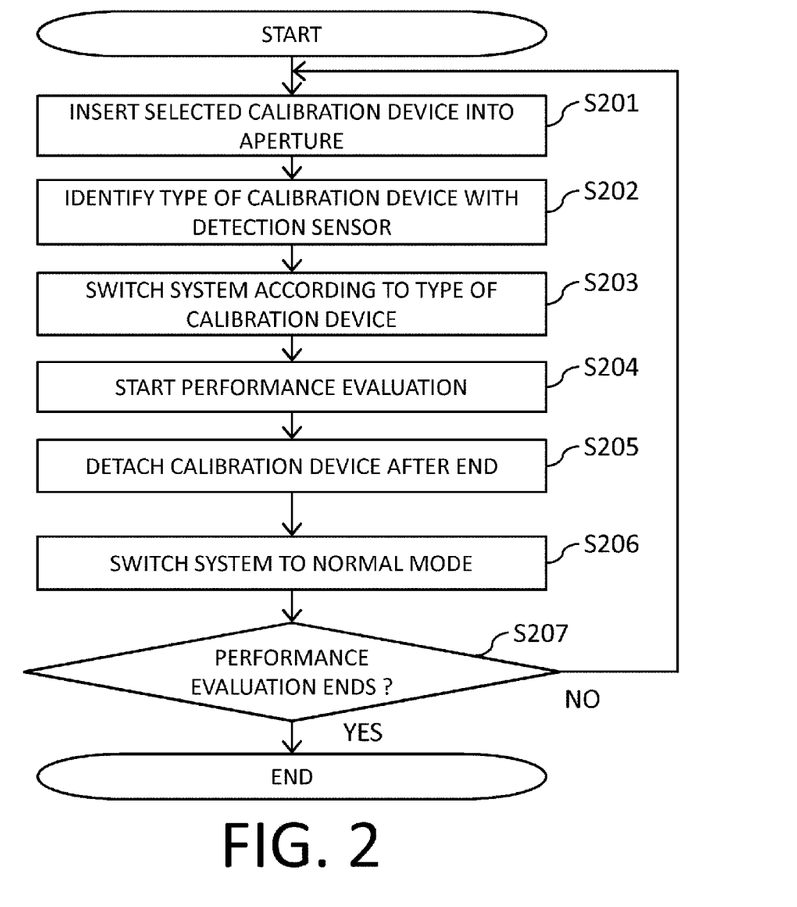
FIG. 2 is a measurement flowchart in the first embodiment.
Figure 3A:
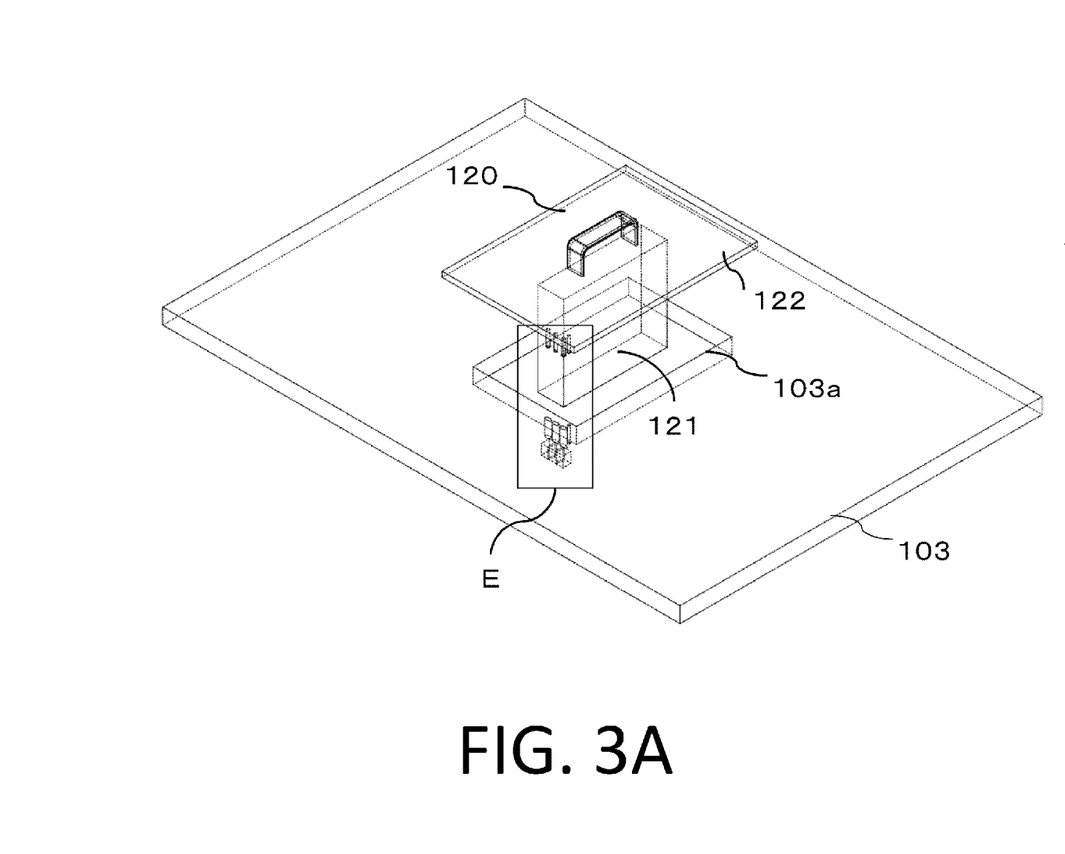
FIGS. 3A and 3B are schematic diagrams showing setting of a calibration device in the photoacoustic diagnostic apparatus in the first embodiment.
Figure 3B:
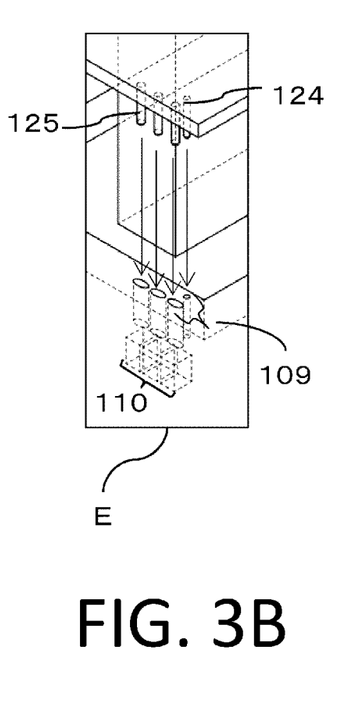

A measurement flow during performance evaluation or calibration for the photoacoustic diagnostic apparatus in this embodiment is shown in FIG. 2. Actions of the measurement flow are explained in detail with reference to FIGS. 1B, 2, and 3A and 3B. FIG. 3A is a schematic diagram showing an example of the calibration device 120 in the first embodiment set in the photoacoustic diagnostic apparatus. FIG. 3B is an enlarged diagram of a portion (indicated by reference sign E) for performing positioning and detection shown in FIG. 3A.

(Step S201) First, the calibration device 120 is selected according to performance evaluation or calibration to be carried out. The selected calibration device 120 is inserted into between the two holding members of the holding unit 104 from the aperture 103a of the housing 103. The positioning pins 124 and the detection pins 125 are individually inserted into round holes and long holes of the positioning unit 109, whereby the calibration device 120 is fixed to the housing 103. A state of the insertion is indicated by an arrow in FIG. 3B.

The evaluation member 121 is set in a predetermined position of the calibration device 120 by the attachment member 123 (not shown in the figure). Therefore, if the calibration device 120 is accurately set, since the evaluation member 121 is accurately positioned, accurate photoacoustic measurement can be performed. The round holes of the positioning unit 109 are formed in substantially the same diameter as the positioning pins 124 to enable the positioning pins 124 to be inserted into the round holes. However, the long holes or the round holes are formed to allow the detection pins 125 to be inserted into the holes with enough room in one direction. Consequently, it is easy to position the calibration device 120.

(Step S202) Subsequently, a type of the calibration device 120 is identified. The number and the arrangement of the detection pins 125 are different depending on a calibration device. Therefore, by arranging the detection members 110 right under the detection pins 125, it is possible to identify which calibration device is set.

Figure 6:
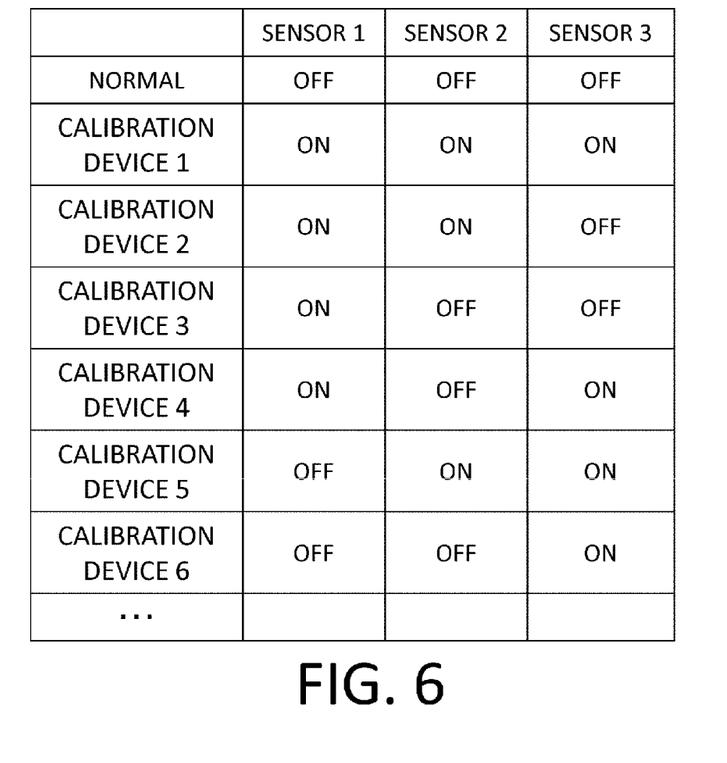
FIG. 6 is a diagram showing an example of correspondence of sensors to six types of calibration devices.

FIG. 6 shows a correspondence relation between a detection member and types of performance evaluation in the case in which six types of calibration devices are provided. It is assumed that the detection member includes three detection members (detection sensors). Two states can be created for each of the detection members according to presence or absence of detection pins. Therefore, it is possible to cope with eight calibration devices in total. The number of detection pins only has to be determined according to the number of types of the calibration devices. It is possible to reduce the number of detection members by using, as the detection members, for example, detection sensors that can detect a plurality of stages according to the depth of pins.

(Step S203) When the detection members 110 detect the type of the calibration device 120 in the preceding step, a signal representing the type of the calibration device 120 is sent to the calculating unit 108. Then, the calculating unit 108 switches the system according to the type of the calibration device 120.

(Step S204) The calculating unit 108 starts performance evaluation or calibration work corresponding to the calibration device 120 and acquires a result of the performance evaluation or calibration work. For example, if content of processing is performance evaluation or calibration that can be performed only by operation on the apparatus side and the operator does not need to intervene, the calculating unit 108 starts up a function to be subjected to the performance evaluation to automatically perform measurement and acquire data. On the other hand, if interaction with the operator is necessary in the performance evaluation or calibration, the calculating unit 108 outputs information for urging the operator to perform operation to the display unit. The calculating unit 108 performs measurement and data acquisition while communicating with the operator.

(Step S205) When the performance evaluation or the calibration ends, the operator detaches the calibration device 120.

(Step S206) When the calibration device 120 is detached, all outputs of the detection sensors of the detection member are turned off and the system is switched to the normal system.

(Step S207) When there is another function that should be subjected to performance evaluation or calibration (No in S207), the processing returns to S201, the calibration device 120 is selected and attached, and the processing explained above is repeated. When all types of performance evaluation and calibration end (Yes in S207), the entire flow ends.

In the photoacoustic diagnostic apparatus in this embodiment, a locking mechanism by the positioning pins 124 and the detection pins 125 is provided. Therefore, it is possible to surely and easily set the calibration device 120 in the positioning unit 109. Since the detection members 110 detect the number and the arrangement of the pins, it is possible to identify a type of the calibration device 120. It is possible to start up the system according to the identified type of the calibration device 120. Therefore, since the apparatus side can recognize the identification of the calibration device 120 without depending on the operator, it is possible to accurately perform various types of performance evaluation of the photoacoustic diagnostic apparatus without complicated work.

<Second Embodiment>

Figure 4A:
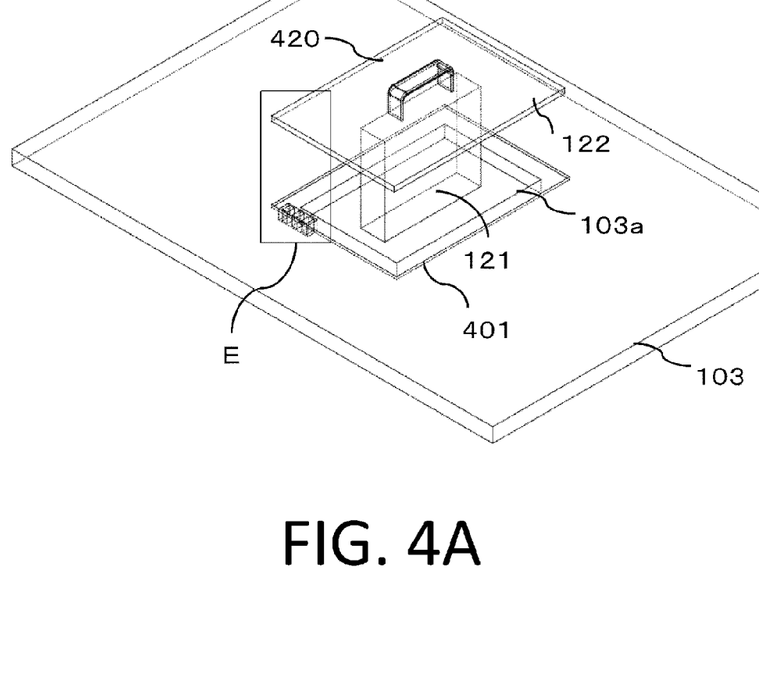
FIGS. 4A and 4B are schematic diagrams showing setting of a calibration device in a photoacoustic diagnostic apparatus in a second embodiment.
Figure 4B:
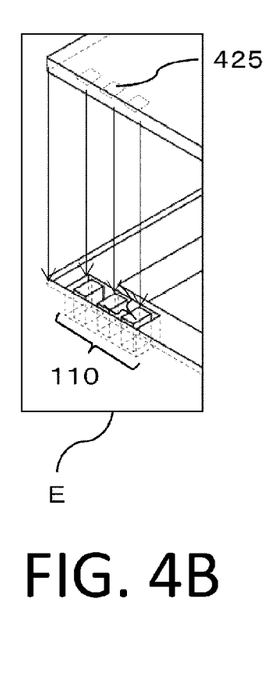

A method of positioning the calibration device according to fitting of the pins is explained in the first embodiment. In a second embodiment, a method different from the method is explained. According to the difference of the method, a method of identifying a type of the calibration device is also different from the method in the first embodiment. That is, in this embodiment, a rectangular groove is formed around an aperture of a housing of a photoacoustic diagnostic apparatus and a setting section of a calibration device is shaped in a rectangular shape. A corner of the rectangular setting section of the calibration device is fit in and struck against the rectangular groove of the aperture, whereby positioning is realized.

FIG. 4A is a schematic diagram showing an example of structure in which a calibration device 420 used for performance evaluation or calibration is set in a photoacoustic diagnostic apparatus. FIG. 4B is an enlarged diagram of the periphery (indicated by reference sign E) of a sensor. The configuration of the photoacoustic diagnostic apparatus in this embodiment is the same as the configuration in the first embodiment except position specifying members of the calibration device and a method of detecting the calibration device with the sensor. Explanation of components same as the components in the first embodiment is omitted.

A positioning unit 401, which is a rectangular groove, is formed in the vicinity of the aperture 103a of the housing 103 to surround an opening. The setting section 122 of the calibration device 420 is formed in a rectangular shape. One corner portion of the setting section 122 and a corner portion of the positioning unit 401 are struck against each other, whereby the calibration device 420 is positioned.

The shape of the setting section of the calibration device and the shape of the groove, which is the positioning unit, of the housing are not limited to rectangular shapes. The setting section and the groove may have any shapes as long as the setting section can be struck against the positioning unit and fixed.

As shown in FIG. 4B, the detection members 110 are provided in the portion of the groove, which is the positioning unit 401. The detection members 110 in this embodiment are a plurality of switches that are turned on and off by a pressure or a load applied from above as indicated by an arrow in the figure. On the other hand, in the setting section 122 of the calibration device 420, switch members 425 are provided in positions where the switch members 425 come into contact with the detection members 110 when the calibration device 420 is attached to the housing 103. A state of ON or OFF can be selected for each of the plurality of switches of the detection members 110 by the switch members 425.

The shapes of the detection members 110 and the switch members 425 can be selected out of various shapes. For example, the switches of the detection members 110 are arranged to slightly extend upward beyond a surface on which the groove is formed around the aperture 103a. This state is represented as switch-off. A state in which the switches of the detection members 110 are pressed by the switch members 425 when the calibration device 420 is attached is represented as switch-on. In this case, the switch of the detection member 110 desired to be kept off can be set in the OFF state by notching or hollowing out the switch member 425 corresponding to the switch. The number and the arrangement of the notches and the hollows are varied according to the calibration device 420. The switches detect the presence of the notches or the like, whereby the calibration device 420 can be identified. The shape of the notches or the hollows may be any shape such as a circular shape or a rectangular shape as long as the sensors can be turned on and off.

A height direction in which the detection members 110 and the switch members 425 are set only has to be set such that the detection members 110 and the switch members 425 are in contact with each other if the switches are switches of a system for detecting a pressure and a load as explained above. Therefore, as in the first embodiment, members projecting from the setting section 122 of the calibration device 420 may be provided as the switch members 425 to press the detection members 110 present below a plane including the groove, which is the positioning unit 401.

As the detection members 110, noncontact detection members that detect light can also be used. When the noncontact detection members are used, even if the detection members 110 and the switch members 425 are not set in contact with each other, it is possible to turn on and off the switches. The detection members 110 detect the outer peripheral section of the setting section 122.

As explained above, in the photoacoustic diagnostic apparatus in this embodiment, it is possible to accurately and easily position the calibration device in the housing and automatically identify a type of the evaluation member provided in the calibration device. Further, it is possible to omit a work process for inserting the positioning pins and the detection pins of the calibration device into the positioning unit and more easily perform positioning.

Third Embodiment

Figure 5A:
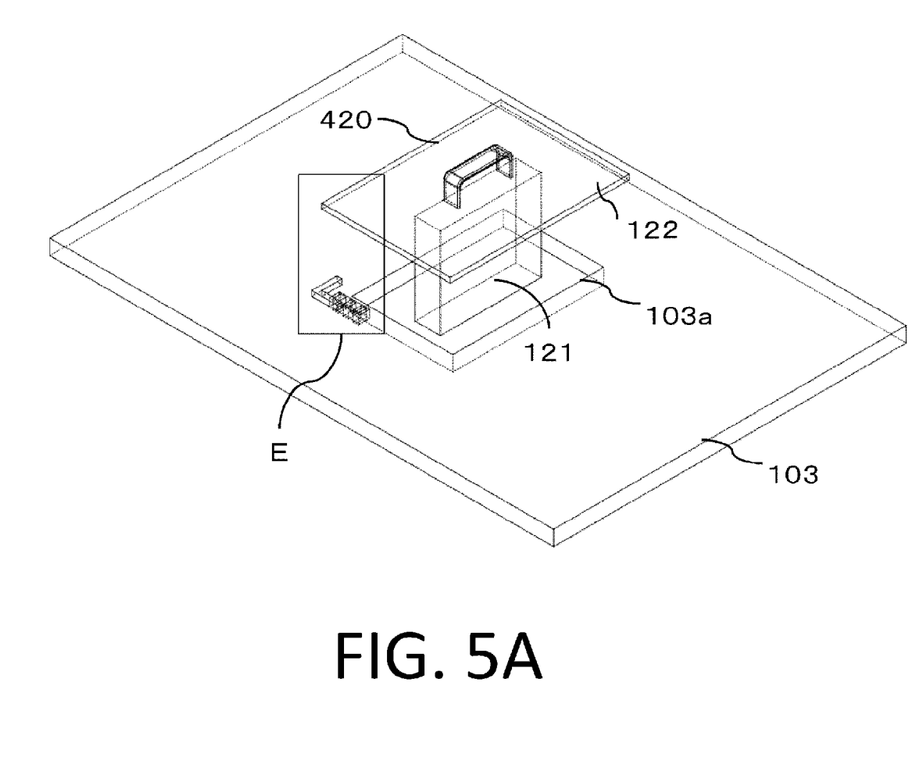
FIGS. 5A and 5B are schematic diagrams showing setting of a calibration device in a photoacoustic diagnostic apparatus in a third embodiment.
Figure 5B:
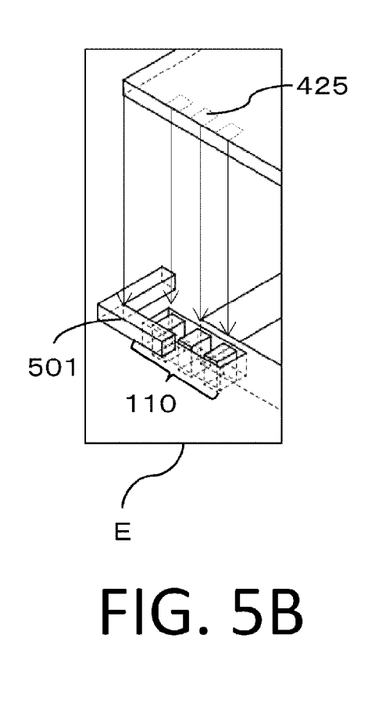

In the second embodiment, the positioning method for striking the rectangular setting section against the rectangular groove of the housing is explained. In a third embodiment, a method different from the method is explained. In this embodiment, a setting section of a calibration device is the same as the setting section in the second embodiment. However, a positioning unit of a photoacoustic diagnostic apparatus is formed by an L-shaped striking member arranged in the vicinity of an aperture of a housing. A corner of the rectangular setting section of the calibration device is struck against the L-shaped member to perform positioning.

FIG. 5A is a schematic diagram showing an example of structure in which the calibration device 420 used for performance evaluation or calibration is set in the photoacoustic diagnostic apparatus. FIG. 5B is an enlarged diagram of the periphery (indicated by reference sign E) of a sensor. The configuration of the photoacoustic diagnostic apparatus in this embodiment is the same as the configuration in the first embodiment except position specifying members of the calibration device and a method of detecting the calibration device with the sensor. Explanation of components same as the components in the first embodiment is omitted.

As shown in FIG. 5B, a striking member, which is a positioning member 501, is provided in the vicinity of the aperture 103a of the housing 103. A corner portion of the setting section 122 and the striking member are struck against each other, whereby the calibration device 420 is positioned. The striking member is desirably formed in an L shape. However, the striking member is not limited to the L shape as long as the striking member and the setting section 122 of the calibration device 420 can be combined and struck against each other. The shape of the setting section 122 and the shape of the striking member only have to correspond to each other to fix the setting section 122 and the striking member.

The shapes and a detecting method for the switch members 425 and the detection members 110 in this embodiment are the same as the shapes and the detecting method explained in the second embodiment. Any detection member such as a pressure sensor, a load sensor, or an optical sensor may be used as long as contact of the setting section 122 from the above indicated by an arrow in FIG. 5B can be detected.

As explained above, in the photoacoustic diagnostic apparatus in this embodiment, it is possible to accurately and easily position the calibration device in the housing and automatically identify a type of the evaluation member provided in the calibration device. Further, it is possible to omit a work process for inserting the positioning pins and the detection pins of the calibration device into the positioning unit and more easily perform positioning.

As explained in the embodiments, according to the present invention, it is possible to facilitate handling of the calibration device for performing performance evaluation or calibration in the photoacoustic diagnostic apparatus. For example, it is possible to accurately and easily perform positioning for the housing of the calibration device. The photoacoustic diagnostic apparatus side easily specifies a type of the calibration device, i.e., content of performance evaluation or calibration and starts up the system for performing processing corresponding to the content. Therefore, it is possible to execute various types of performance evaluation without mistakes. Further, since the apparatus side can recognize identification of the positioning and the calibration device without depending on the operator, it is possible to reduce complication of work.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-053181, filed on Mar. 9, 2012, which is hereby incorporated by reference herein its entirety.

What is claimed is:

1. An object information acquiring apparatus that receives an acoustic wave generated from an object, on which light is irradiated, and generates property information of an inside of the object, the object information acquiring apparatus comprising:
    a housing including an aperture into which, when the acoustic wave is received, the object, which is a part of an examinee, is inserted and, when performance evaluation for the object information acquiring apparatus is performed, a calibration device corresponding to a type of the performance evaluation is inserted, the housing being capable of holding the examinee;
    a holding unit configured to hold the object;
    a positioning unit configured to specify an attachment position of the calibration device correspondingly to a position specifying member provided in the calibration device inserted into the aperture; and
    a detecting unit configured to detect the type of the performance evaluation performed using the calibration device inserted into the aperture.

2. The object information acquiring apparatus according to claim 1, further comprising a calculating unit configured to perform the performance evaluation for the object information acquiring apparatus, wherein
    the calculating unit switches content of processing according to the type of the performance evaluation which is detected by the detecting unit.

3. The object information acquiring apparatus according to claim 1, wherein
    a type specifying member corresponding to the type of the performance evaluation can be attached to the calibration device, and
    the detecting unit detects the type of the performance evaluation using the type specifying member.

4. The object information acquiring apparatus according to claim 1, wherein
    the position specifying member of the calibration device is a pin projecting from the calibration device, and
    the positioning unit of the object information acquiring apparatus is a hole into which the pin can be inserted.

5. The object information acquiring apparatus according to claim 4, wherein
    the pin serving as the position specifying member of the calibration device is used also as the type specifying member of the calibration device, arrangement of the pin being different depending on the type of the performance evaluation, and
    the detecting unit of the object information acquiring apparatus detects a state in which the pin is inserted into the hole, which serves the positioning unit of the object information acquiring apparatus.

6. The object information acquiring apparatus according to claim 1, wherein
    the positioning unit of the object information acquiring apparatus is a groove formed around the aperture, and
    the position specifying member of the calibration device is a member that fits in the groove serving as the positioning unit.

7. The object information acquiring apparatus according to claim 6, wherein
    the positioning unit is a rectangular groove provided on a surface on which the housing holds the examinee, and
    the position specifying member is a rectangular member that fits in the positioning unit.

8. The object information acquiring apparatus according to claim 6, wherein
    the type specifying member of the calibration device is a hole or a notch provided on a surface, which is in contact with the positioning unit, of the position specifying member, arrangement of the hole or the notch being different depending on the type of the performance evaluation, and
    the detecting unit of the object information acquiring apparatus is formed of a plurality of switches which detect the presence of the hole or the notch.

9. The object information acquiring apparatus according to claim 1, wherein an evaluation member corresponding to the type of the performance evaluation can be attached to the calibration device.

10. The object information acquiring apparatus according to claim 9, wherein
    the calibration device is used to evaluate performance of irradiation of light on the object, and
    the evaluation member can measure a state of the irradiated light.

11. The object information acquiring apparatus according to claim 10, wherein the evaluation member measures an amount of the light irradiated on the object.

12. The object information acquiring apparatus according to claim 10, wherein the calibration device is used to evaluate whether the light irradiated on the object matches a safety standard.

13. The object information acquiring apparatus according to claim 9, wherein
the holding unit presses and holds the object with two holding members, and
the evaluation member can measure a pressure when the object is held.

14. The object information acquiring apparatus according to claim 9, wherein
the evaluation member is a phantom that simulates a biological tissue and is made of a known material, and
the calibration device is used to evaluate performance of generation of the property information by the object information acquiring apparatus.

15. A calibration device for performing performance evaluation for an object information acquiring apparatus that receives an acoustic wave generated from an object, on which light is irradiated, and generate property information of an inside of the object, the calibration device being inserted from an aperture provided in a housing of the object information acquiring apparatus, the calibration device comprising:
a position specifying member configured to specify a position of the calibration device in the object information acquiring apparatus, correspondingly to a positioning unit provided in the object information acquiring apparatus;
an evaluation member corresponding to a type of the performance evaluation; and
a type specifying member that can be attached according to the type of the performance evaluation and that corresponds to a detecting unit provided in the object information acquiring apparatus.

\* \* \* \* \*